United States Patent [19]

Shukuzaki et al.

[11] Patent Number: 5,266,321
[45] Date of Patent: Nov. 30, 1993

[54] OILY MAKE-UP COSMETIC COMPRISING OIL BASE AND SILICONE GEL COMPOSITION

[75] Inventors: Koichi Shukuzaki; Kazuhiro Suzuki; Miki Yamazoe, all of Tokyo, Japan

[73] Assignee: Kobayashi Kose Co., Ltd., Tokyo, Japan

[21] Appl. No.: 852,496

[22] Filed: Mar. 17, 1992

Related U.S. Application Data

[63] Continuation of Ser. No. 330,059, Mar. 29, 1989, abandoned.

[30] Foreign Application Priority Data

Mar. 31, 1988 [JP] Japan .................................. 63-80018
Apr. 4, 1988 [JP] Japan .................................. 63-81308
Apr. 4, 1988 [JP] Japan .................................. 63-81309

[51] Int. Cl.$^5$ .............. A61K 7/02; A61K 7/021; A61K 7/025; A61K 7/027
[52] U.S. Cl. .................................. 424/401; 424/63; 424/64; 424/DIG. 5; 514/844; 514/845; 514/937; 514/947
[58] Field of Search ................. 424/401, 63, 64, 78, 424/81, DIG. 5; 514/844-847, 937, 938, 947

[56] References Cited

U.S. PATENT DOCUMENTS

| | | | |
|---|---|---|---|
| 4,698,386 | 10/1987 | Fujimoto | 524/862 |
| 4,699,780 | 10/1987 | Jennings et al. | 424/64 |
| 4,782,095 | 11/1988 | Gum | 514/937 |
| 4,792,444 | 12/1988 | Fukasawa et al. | 424/64 |
| 4,795,631 | 1/1989 | Sheehan | 424/64 |
| 4,801,445 | 1/1989 | Fukui | 514/844 |
| 4,801,447 | 1/1989 | Gum | 514/844 |
| 4,820,510 | 4/1989 | Arraudeau et al. | 424/69 |
| 4,857,307 | 8/1989 | Suss et al. | 424/69 |
| 4,954,532 | 9/1990 | Elliott | 514/846 |

Primary Examiner—Thurman K. Page
Assistant Examiner—E. Webman
Attorney, Agent, or Firm—Oblon, Spivak, McClelland, Maier & Neustadt

[57] ABSTRACT

An oily make-up cosmetic composition which can provide an excellent feeling upon use, a superior make-up effect, and good stability over time is disclosed. The cosmetic composition is normally of a solid form, and comprises a silicone gel composition and a cosmetic powder material, both dispersed in an oil base. The composition may further comprises an aqueous gel of water-soluble polymer containing glycerine.

13 Claims, No Drawings

OILY MAKE-UP COSMETIC COMPRISING OIL BASE AND SILICONE GEL COMPOSITION

This application is a Continuation of application Ser. No. 07/330,059, filed on Mar. 29, 1989, now abandoned.

BACKGROUND OF THE INVENTION

1. Field of the Invention

This invention relates to an oily make-up cosmetic. More particularly, this invention relates to an oily make-up cosmetic, especially of a solid form, which comprises a silicone gel composition and a cosmetic powder material, both dispersed in an oil base. The invention also relates to an oily make-up cosmetic which further comprises an aqueous gel of water-soluble polymer containing glycerine. The oily make-up cosmetic of this invention gives an excellent feeling upon use, provides a superior make-up effect, and exhibits good stability over time.

2. Description of the Background:

Oily make-up cosmetics are widely used because of their excellent characteristics in terms of adherence to the skin, skin covering capability, and water-repellency of the cosmetic film. In the preparation of oily make-up cosmetics, an oil base which comprises a semi-solid or liquid oil, or an oil base prepared by the gelation of these oils by the addition of an oil gelling agent, is conventionally used as a base material. A cosmetic powder material is mixed with and dispersed into the oil base. The mixture is then solidified or molded to produce an oily make-up cosmetic.

These conventional oily make-up cosmetics, however, have drawbacks of providing sticky and oily feelings, and of having only insufficient extendibility or spreadability, because of their higher oil content.

Various attempts have been undertaken in order to overcome such drawbacks. Such attempts include (i) formulating water or water-soluble components to convert the composition into a W/O type emulsion, (ii) decreasing the amount of oil, and (iii) formulating a less oily oil component such as a low viscosity silicone oil.

W/O emulsion type make-up cosmetics, although they may provide a fresh feeling, have a drawback of losing their water content over time through vaporization. Extensive studies have been undertaken in order to eliminate this drawback. No such efforts, however, have been successful in completely preventing the water vaporization. Decreasing the amount of oil or formulating a less oily oil component did not necessarily give a sufficient solution to the problem of the oily feeling which is inherent to an oil base material. Although a low viscosity silicone oil gives a less sticky, fresh feeling by itself, it does not provide such a fresh feeling when formulated into a conventional oil base material. In addition, since a low viscosity silicone oil falls short of mutual solubility or compatibility, with an oil base material, difficulty is encountered in securing the stability of the cosmetic into which this compound is formulated.

Therefore, the development of an oily make-up cosmetic, which is free from drawbacks of stickiness or oiliness, while providing a fresh feeling upon use and maintaining excellent characteristics inherent to oily make-up cosmetics, has been desired.

The present inventors have conducted extensive studies in order to overcome the above-mentioned problems. As a result, the inventors have found that an oily make-up cosmetic which is less sticky and provides not only a fresh, smooth feeling to the skin but also superior make-up effects could be obtained by dispersing a silicone gel composition which is prepared by encompassing a low viscosity silicone oil into the structure of a crosslinked organopolysiloxane polymeric compound [Component (B)] and a cosmetic powder material [Component (C)] into an oil base. The inventors have further found that an oily make-up cosmetic providing even better make-up effects and superior stability could be obtained by formulating, in addition to the Components (B) and (C), an aqueous gel of water-soluble polymer containing glycerine [Component (D)].

SUMMARY OF THE INVENTION

Accordingly, an object of this invention is to provide an oily make-up cosmetic comprising:

(A) an oil base which comprises (i) a semi-solid or liquid oil and (ii) a solid oil, an oil gelling agent, or a mixture thereof, (B) a silicone gel composition which comprises a partially crosslinked organopolysiloxane polymeric compound and a low viscosity silicone oil, and (C) a cosmetic powder material.

Another object of this invention is to provide an oily make-up cosmetic comprising:

(A) an oil base which comprises (i) a semi-solid or liquid oil and (ii) a solid oil, an oil gelling agent, or a mixture thereof, (B) a silicone gel composition which comprises a partially crosslinked organopolysiloxane polymeric compound and a low viscosity silicone oil, (C) a cosmetic powder material, and (D) an aqueous gel of acrylic water-soluble polymer containing glycerine, said polymer exhibiting a viscosity increase by the addition of an alkali.

Other objects, features and advantages of the invention will hereinafter become more readily apparent from the following description.

DETAILED DESCRIPTION OF THE INVENTION AND PREFERRED EMBODIMENTS

Oil bases which may be used in this invention as Component (A) comprises (i) a semi-solid or liquid oil and (ii) a solid oil, an oil gelling agent, or a mixture of a solid oil and an oil gelling agent.

Various oils which are conventionally used for cosmetics can be used as a semi-solid or liquid oil without special limitations. Such oils includes mineral oils, plant oils, animal oils, higher fatty acids, higher fatty acid esters, higher alcohols, and the like. Specific examples are liquid paraffin, squalane, castor oil, isopropyl myristate, isopropyl palmitate, lanoline, petrolatum, olive oil, jojoba oil, macademia nuts oil, mink oil, turtle oil, almond oil, safflower oil, avocado oil, octyldodecyl myristate, cetyl 2-ethylhexanoate, glycerine fatty acid esters such as 2-ethylhexanoic acid triglyceride, diglycerine fatty acid esters such as diglyceryl isostearate, propylene glycol fatty acid esters such as propylene glycol dicaprate, dipentaerythritol fatty acid esters, oleic acid, oleyl alcohol, and the like.

As a solid oil, various solid oils which are allowed to be used for cosmetics and having a melting point of 40° C. or higher can be used without specific limitations. Such a solid oil may be a hydrocarbon, wax, hydrogenated oil, higher fatty acid, higher alcohol, or the like.

Specific examples include solid paraffin wax, serecin wax, microcrystalline wax, carnauba wax, candelilla wax, bees wax, japan wax, spermaceti, polyethylene wax, hydrogenated castor oil, pentaerythritol rhodinate, stearic acid, lauric acid, myristic acid, behenic acid, cetyl alcohol, stearyl alcohol, lauryl alcohol, and the like.

An oil gelling agent assists to gel the above oil components and to adjust the hardness of cosmetics. Another purpose of formulating an oil gelling agent is to provide the cosmetics with suitable extendibility on the skin. Any oil gelling agents known in the art as cosmetic ingredients may be used in this invention. Examples of such oil gelling agents are mineral clays, e.g. organic modified montmorillonite clay; starch fatty acid esters, e.g. starch-derived fatty acid esters having an average polymerization degree of 10–50; lipophilic sucrose fatty acid esters, e.g. a mixture of sucrose fatty acid esters comprising those with a fatty acid carbon atom content of 12 or more and having a monoester content of 10% by weight or less; N-acylamino acid derivatives such as amides, esters, and amine salts, e.g. lauroyl glutamic acid dibutyl amide, dilauroyl lysine stearyl amine salt; metallic soaps, e.g. aluminum 12-hydroxystearate, calcium stearate, calcium palmitate, and the like.

The oil base of this invention can be prepared by mixing these solid oils and oil gelling agents with the aforementioned semi-solid or liquid oil. In this instance, either one type of solid oil or oil gelling agent can be used, or two or more types among from solid oils and oil gelling agents may be used in combination. A preferable amount of the solid oils and oil gelling agents to be formulated is 5–40% by weight of the oil base.

The silicone gel composition which is the (B) component of the oily make-up cosmetic of the present invention comprises (a) a partially crosslinked organopolysiloxane polymeric compound and (b) a low viscosity silicone oil. This silicone gel composition is structured such that silicone oil (b) is encompassed by polymeric compound (a).

The partially crosslinked organopolysiloxane polymeric compound (a) which can be used may include, for example, an organopolysiloxane polymeric compound which is insoluble in benzene and has a three dimensional crosslinked structure in which benzene of an equivalent or more amount of the organopolysiloxane polymeric compound itself may be contained. Such a polymeric compound can be prepared by the crosslinking reaction of organopolysiloxane, may contain three dimensional crosslinking structures, and consists of $R_2SiO$ and $RSiO_{1.5}$ units. The polymeric compound may also contain $R_3SiO_{0.5}$, $SiO_2$, or both.

Given as examples of R in the above organopolysiloxane constituting unit are hydrogen atom an alkyl group such as methyl, ethyl, propyl, or the like, an aryl group such as phenyl, tolyl, or the like, and an unsaturated aliphatic group such as vinyl group. The organosiloxane unit may contain either one type of R, or two or more different types of R.

In order for the organopolysiloxane to be insoluble in benzene and to take a three dimensional crosslinked structure in which benzene of an equivalent or more amount of the organopolysiloxane polymeric compound itself may be contained, it is essential that the ratio of either $RSiO_{1.5}$ or $SiO_2$, or $RSiO_{1.5}$ plus $SiO_2$, and either $R_2SiO$ or $R_3SiO_{0.5}$, or $R_2SiO$ plus $R_3SiO_{0.5}$, be in a suitable range. If the amount of either $RSiO_{0.5}$, or $SiO_2$, or $RSiO_{1.5}$ plus $SiO_2$, is too small in proportion to the amount of either $R_2SiO$ or $R_3SiO_{0.5}$, or $R_2SiO$ plus $R_3SiO_{0.5}$, the organopolysiloxane does not take a sufficient degree of three dimensional crosslinked structure and is soluble in benzene. This type of organopolysiloxane cannot be used for the purpose of this invention, even though it may contain a crosslinked structure. On the other hand, if the amount of either $RSiO_{1.5}$ or $SiO_2$, or $RSiO_{1.5}$ plus $SiO_2$, is too large in proportion to the amount of either $R_2SiO$ or $R_3SiO_{0.5}$, or $R_2SiO$ plus $R_3SiO_{0.5}$, the crosslinked structure of organopolysiloxane becomes so hard that it only contains benzene in an amount less than the amount of organopolysiloxane itself, even though it is insoluble in benzene. This type of organopolysiloxane cannot be used for the purpose of this invention, since it separates and is released from an organopolysiloxane-low viscosity silicone oil mixture.

The ratio of the $R_2SiO$ unit to the $RSiO_{1.5}$ unit in an organopolysiloxane polymeric compound which is insoluble in benzene and may contain an equivalent or more amount of benzene can not be strictly specified because of significant involvement of the molecular weight magnitude of the whole organopolysiloxane polymeric compound, as another factor. In practice, however, a ratio of 1:1 to 30:1 gave good results. If the amount of the $RSiO_{1.5}$ unit is in a higher side above this ratio, the organopolysiloxane polymeric compound becomes too hard to contain the equivalent amount of benzene in it. This type of organopolysiloxane does not sufficiently swell when it is mixed with a low viscosity silicone oil. Silicone oil separates and is discharged from the mixture. This impairs the stability of the composition. On the other hand, if the amount of the $R_2SiO$ unit is in a higher side above the above-mentioned ratio, the structural viscosity properties of the organopolysiloxane is damaged. Because of these reasons, the above-mentioned range of the organopolysiloxane structural unit ratio is desirable in order to produce a superior silicone gel composition which is both soft and stable.

An organopolysiloxane polymeric compound, insoluble in benzene and having a three dimensional crosslinked structure which may contain benzene in an equivalent or more amount of the weight of itself, can be prepared by various methods. Examples of such methods include:

(1) A dehydrogenation-condensation reaction of an organohydrogenpolysiloxane having at least 2 hydrogen atoms which are combined with a silicon atom in one molecule. The dehydrogenation-condensation reaction is carried out in the presence of a catalytic amount of an alcoholic aqueous solution of an alkali metal hydroxide and under heating.

(2) A dehydrogenation-condensation reaction of an organohydrogenpolysiloxane having at least 2 hydrogen atoms which are combined with a silicon atom in one molecule and an organopolysiloxane having at least 2 hydroxyl groups which are combined with a silicon atom in one molecule. This dehydrogenation-condensation reaction is carried out in the presence of a catalytic amount of an alkali metal hydroxide or a platinum compound and under heating.

(3) A dehydration-condensation reaction of an organopolysiloxane having at least 2 hydroxyl groups which are combined with a silicon atom in one molecule. The dehydration-condensation reaction is carried out in the presence of a catalytic amount of an alkali metal hydroxide or an organo-tin compound and under heating.

(4) A dealcohol reaction of an organopolysiloxane having at least 2 hydroxyl groups which are combined with a silicon atom in one molecule and another organopolysiloxane having at least 2 alkoxy groups which are combined with a silicon atom in one molecule. The dealcohol reaction is carried out in the presence of a catalytic amount of an alkali metal hydroxide or an organo-tin compound and under heating.

All of these methods can easily produce an organopolysiloxane polymeric compound which is insoluble in benzene and has a three dimensional crosslinked structure capable of containing benzene of an equivalent or more amount of the organopolysiloxane polymeric compound itself.

As another example of a partially crosslinked organopolysiloxane polymeric compound (a), an organopolysiloxane polymeric compound which is insoluble in but sufficiently swells in silicone oil is given. This organopolysiloxane polymeric compound is prepared by the addition polymerization of (i) an organo-hydrogenpolysiloxane and (ii) an organopolysiloxane having unsaturated aliphatic groups, and contains a partial three dimensional crosslinked structure.

The organohydrogenpolysiloxane (i) used in the addition polymerization is comprised of units $HSiO_{1.5}$, $RSiO_{1.5}$, $RHSiO$, $R_2SiO$, $R_2HSiO_{0.5}$, $R_3SiO_{0.5}$, and the like. This compound may take either of linear, branched, and cyclic molecular structures, and contains at least 2 hydrogen atoms which are combined with a silicon atom in one molecule. For the better control of the reaction of producing the organopolysiloxane polymeric compound, an organohydrogenpolysiloxane used is desirable to have a linear structure. The hydrogen atom bonded to the silicon atom, i.e., H in —SiH bond, of the organohydrogenpolysiloxane molecule is usually contained within the molecular chain. It may, however, be at the molecular chain terminal. A preferable amount of the —SiH bond is usually 1-20 mol% when the molecular structure is linear or branched, and 1-50 mol% when the molecular structure is cyclic. A preferable organohydrogenpolysiloxane is that contains 50 mol% or more methyl group of organic groups other than —SiH bond.

The above-mentioned organopolysiloxane (ii) having unsaturated aliphatic groups which is used in the addition polymerization reaction is one that contains at least 2 unsaturated aliphatic groups which are bonded to a silicon atom in one molecule. Given as examples of this type of organopolysiloxane are those containing vinyl groups or allyl groups. Usually, an organovinylpolysiloxane containing vinyl group is used. A specific example of organovinylpolysiloxane is that contain units $(CH_2=CH)SiO_{1.5}$, $RSiO_{1.5}$, $R(CH=CH_2)SiO$, $R_2SiO$, $R_2(CH=CH_2)SiO_{0.5}$, $R_3SiO_{0.5}$, and the like. The molecular structure may be either linear, branched, or cyclic, and contains at least 2 unsaturated aliphatic groups, e.g. vinyl group, in one molecule. For the better control of the reaction of producing the organopolysiloxane polymeric compound, an organopolysiloxane used is desirable to have a linear structure. This type of organovinylpolysiloxane usually has a linear structure having dimethylvinylsilyl groups at its both ends of the molecule. The vinyl group, however, be within the molecular chain. A preferable amount of the vinyl group is usually 1-20 mol% when the molecular structure is linear or branched, and 1-50 mol% when the molecular structure is cyclic. A preferable organovinylpolysiloxane is that contains 50 mol% or more methyl group of organic groups other than vinyl group.

It is essential for the organohydrogenpolysiloxane (i) and organopolysiloxane having unsaturated aliphatic groups (ii), e.g. organovinylpolysiloxane, to produce an addition polymerization compound having a three dimensional structure in part that these organopolysiloxanes (i) and (ii) contain at least 2 reactive groups, i.e., hydrogen atoms bonded to a silicon atom or a vinyl group. If the amount of these reactive groups contained in organopolysiloxanes (i) or (ii) is greater than 20 mol%, in the case where organopolysiloxanes have linear or branched structures, or is greater than 50 mol%, in the case where organopolysiloxanes have a cyclic structure, the polymers produced become stiff. In addition, a low viscosity silicone oil tends to be encompassed by the three dimensional structure of such polymers only with difficulty, the oil separating and being discharged from the mixture, thus resulting in a less stable product. Conversely, if the content of the reactive groups is less than 1%, the structural viscosity properties of the organopolysiloxane tends to be damaged. Because of these reasons, although not restrictive, the amount of the reactive groups contained in organopolysiloxanes (i) or (ii) is 1-20 mol%, in the case where organopolysiloxanes have linear or branched structures, or 1-50 mol%, in the case where organopolysiloxanes have a cyclic structure, in order to produce a superior silicone gel composition which is both soft and stable.

Given as examples of the organic group R in the constituting unit of the above organohydrogenpolysiloxane (i) are an alkyl group such as methyl, ethyl, propyl, butyl, or the like, an aryl group such as phenyl, tolyl, or the like, or cyclohexyl group. R may also be a substituted monovalent hydrocarbon group, other than unsaturated aliphatic hydrocarbon groups such as vinyl group. The substitution group may be halogen atom, cyano group or the like.

A typical example of such an organohydrogenpolysiloxane is a methylhydrogenpolysiloxane containing units $(CH_3)_3SiO_{2/1}$—, —$[(CH_3)_2SiO]_p$—, —$[CH_3HSiO]_q$—, and —$Si(CH_3)_3$, wherein p is a value of 10-500 and q is a value of 2-50.

The organic group R contained in organovinylpolysiloxane, which is an organopolysiloxane having unsaturated aliphatic groups (ii), have the same meaning as the R for organohydrogenpolysiloxanes. A typical example of such an organovinylpolysiloxane is that containing units $(CH_2=CH)(CH_3)_2SiO$—, —$[(CH_3)_2SiO]_r$—, and —$OSi(CH_3)_2(CH=CH_2)$, wherein r is a value of 10-100, or that containing units $(CH_3)_3SiO$—, —$[(CH_3)_2SiO]_m$—, —$[(CH=CH_2)CH_3SiO]_n$—, and —$Si(CH_3)_3$, wherein m is a value of 10-500 and n is a value of 2-50. These organovinylpolysiloxanes are suitable material and may be used either individually or as a mixture.

The addition polymerization reaction of the organohydrogenpolysiloxane (i) and organopolysiloxane having unsaturated aliphatic groups (ii) can be carried out according to a commonly known method. For example, a target organopolysiloxane polymeric compound which is insoluble in a silicone oil can be easily prepared by reacting an organohydrogenpolysiloxane and an organovinylpolysiloxane, at a proportion such that the molar ratio of SiH group and vinyl group be in a range of 1/3-3/1, under heating while stirring in the presence of a platinum or palladium addition polymerization catalyst. An especially preferable addition polymerization catalyst is chloroplatinic acid described in Japanese Patent Publication No 9969/1958.

As a low viscosity silicone oil, which is another component, (b), of the silicone gel composition of the present invention, any silicone oils having a viscosity of about 50 cs or less can be suitably used, although this viscosity requirement is not restrictive. When a large amount of silicone oil is to be used the higher the viscosity is, the more oily and worse feeling is provided by the make-up cosmetic. Given as specific examples of low viscosity silicone oils are low-polymerization, linear dimethylpolysiloxane, methylphenylpolysiloxane, octamethylcyclotetrasiloxane, decamethylcyclopentasiloxane, and the like. Either one kind of these compounds, or two or more kinds suitably selected from the group may be used for the purpose of this invention.

A silicone gel composition, which is component (B) of the present invention, can easily be prepared by mixing and sufficiently kneading to swell the above-mentioned partially crosslinked organopolysiloxane polymeric compound (a) and a low viscosity silicone oil (b). Here, the mixing ratio by weight of (a) and (b) is 5/95 to 30/70, and preferably 10/90 to 25/75.

If the amount of a partially crosslinked organopolysiloxane polymeric compound is too small, excessive amount of a low viscosity silicone oil renders the composition fluid-viscous and prevents it from maintaining a proper gel structure. On the other hand, if the amount of the organopolysiloxane polymeric compound is too large, it becomes difficult to produce a soft gel composition.

Various kinds of cosmetic powder materials can be used without special limitation as the (C) component. It may be a body pigment, inorganic white pigment, inorganic colored pigment, organic powder, pearling agent, or the like. Specific examples are talc, kaolin, mica, magnesium carbonate, calcium carbonate, magnesium silicate, aluminum magnesium silicate, silica, titanium dioxide, zinc oxide, red iron oxide, yellow iron oxide, black iron oxide, ultramarine blue, tar pigment, nylon powder, polyethylene powder, methylacrylate powder, styrene powder, polytetrafluoroethylene powder, silk powder, and crystalline cellulose, starch, titanated mica, iron oxide titanated mica, bismuth oxychloride, or the like.

An aqueous gel of acrylic water-soluble polymer containing glycerine, which is the (D) component of this invention, is an aqueous gel of a crosslinked polyacrylic water-soluble polymer containing 30-70% by weight of glycerine.

The so-called water-soluble viscosity increase-in-alkali type polymer which form a gel by the neutralization with an alkali can be used as a crosslinked polyacrylic water-soluble polymer. Given as examples of this type of polymers are homopolymers or copolymers of acrylic acid and methacrylic acid, carboxyvinyl polymer, salts of these polymers, and the like. An alkali for neutralizing the water-soluble polymers may be an inorganic or organic base such as, for example, sodium hydroxide, potassium hydroxide, ammonium hydroxide, triethanolamine, L-arginine, or the like.

The amount of the crosslinked polyacrylic water-soluble polymer used in the gel depends upon the type of polymer. Usually, the amount is in the range of 0.2-3.0% by weight.

A preferable proportion of components (A)-(D) used for preparing an oily make-up cosmetic of this invention is as follows:

|  | Preferable Range (wt %) | Especially Preferable Range (wt %) |
| --- | --- | --- |
| Oil base [Component (A)] | 30-80 | 40-70 |
| Silicone gel composition [Component (B)] | 10-40 | 20-30 |
| Cosmetic powder [Component (C)] | 1-40 | 15-25 |
| Aqueous gel of water-soluble polymer [Component (D)] | 5-30 | 10-25 |

A preferable proportion of component (A) to component (B) in terms of ratio by weight is 55/45 to 95/5, with especially preferable range being 55/45 to 65/35. If the amount of component (B) is too large, the stat in which component (B) is dispersed in component (A) can not be maintained. If the amount of component (B) is too small, the effect of this invention can be obtained only insufficiently.

It is desirable that an oily make-up cosmetic comprising components (A), (B), and (C), but not (D), does not substantially contain water.

In an oily make-up cosmetic which comprises component (D), if the amount of the component (D) is 30% by weight or more, the consistency or firmness of the product can be maintained only with difficulty. On the other hand, if the amount of the component (D) is less than 5% by weight, the effect of formulating this component, e.g. providing a refreshing feeling, cannot be obtained. It is desirable to formulate components (A) and (B) in an amount greater than the amount of component (D).

In the preparation of an oily make-up cosmetic of this invention, components (A)-(C) or (A)-(D), i.e., an oil base, a silicone gel composition, and a cosmetic powder material, or an oil base, a silicone gel composition, a cosmetic powder material; and an aqueous gel of acrylic water-soluble viscosity increase-in-alkali type polymer containing glycerine, are mixed homogeneously according to a conventional method. There is no specific restriction as to the order by which the components are added, inasmuch as the silicone gel composition, cosmetic powder material, and aqueous gel of water-soluble polymer are homogeneously dispersed into the oil base.

Besides these essential components, perfumes, antiseptics, UV absorbers, surface active agents, anti-oxidants, polymers, and the like can be formulated into the oily make-up cosmetic of this invention, to the extent that the effects of this invention are not impaired.

The oily make-up cosmetic of this invention may be applied to a foundation, eye-shadow, face powder, lip stick, and the like. It may take various forms including a solid, stick, and the like.

In the oily make-up cosmetic comprising components (A), (B), and (C) of this invention, a silicone gel composition and a cosmetic powder material are dispersed in an oil base. A low viscosity silicone oil which is formulated in the silicone gel composition is present encompassed by a three dimensional crosslinked structure of an organopolysiloxane polymeric compound. Since the gel structure of this silicone gel composition is destroyed very easily even by a small external force, the low viscosity silicone oil which is encompassed oozes out from the oily make-up cosmetic by a friction force exerted by an applicator or by a force applied when it is extended onto the skin. Thus, the oily make-up cosmetic comprising components (A), (B), and (C) of this invention possess characteristics specific to oily type cosmetics in terms of adherence, covering capability, water-repellency of the cosmetic films, and the like. In addition, this oily make-up cosmetic is free from a sticky, oily feeling, and provides smooth, slippery, and fresh feelings. This cosmetic does not produce an oily, glittering film. Rather, it can provide a natural, well-finished make-up which is kept long.

In the oily make-up cosmetic comprising components (A), (B), (C), and (D) of this invention, glycerine and water, which are formulated as components of an aqueous gel of water-soluble polymer (D), function as aqueous base and are present, together with the water-soluble viscosity increase-in-alkali type acrylic polymer, as droplets in the oily cosmetic. Because of this, the make-up effects of this cosmetic are even better than the above-mentioned oily make-up cosmetic comprising components (A), (B), and (C). Since water is stably hold in the cosmetic without being dissipated through vaporization, the cosmetic is kept stable over time and is free from a heavy, oily feeling which is often the case with an oily make-up cosmetic.

Other features of the invention will become apparent in the course of the following description of the exemplary embodiments which are given for illustration of the invention and are not intended to be limiting thereof.

EXAMPLES

Reference Example 1

An appropriate amount of 1% aqueous solution of potassium hydroxide (ethanol/water=2/1) was added to dimethylmethylhydrogenpolysiloxane with trimethylsilyl terminal groups [Molecular weight: 2,300; $CH_3HSiO/(CH_3)_2SiO = \frac{1}{4}$ (molar ratio)]. The mixture was heated while refluxing to polymerize. The polymer thus produced was washed with water to remove the alkali and allowed to stand to dry, thus obtaining a silicone polymeric compound which is insoluble in benzene and capable of containing benzene in an amount of 180% of its weight.

Two (2) parts by weight of this silicone polymeric compound and 8 parts by weight of dimethylpolysiloxane (viscosity: 5 cs) were mixed to disperse each other. The product was thoroughly kneaded by a triple roller to swell, thus producing a silicone gel composition.

Reference Example 2

A silicone gel composition was produced in the same manner as in Reference Example 1, except that organohydrogenpolysiloxane used in this example was dimethylmethylhydrogenpolysiloxane with trimethylsilyl terminal groups [Molecular weight: 4,800; $CH_3HSiO/(CH_3)_2SiO = 3/9.6$ (molar ratio)].

Reference Example 3

1,790 g of dimethylmethylhydrogenpolysiloxane with trimethylsilyl terminal groups (Average molecular weight: 2,340; Si—H: 4.5 mol%) and 710 g of dimethylpolysiloxane with dimethylvinylsilyl terminal groups (Average molecular weight: 930; vinyl group: 7.7 mol%) were placed in a planetary mixer with an internal volume of 5 l and mixed with stirring.

After the addition of 0.5 g of 2% chloroplatinic acid solution in isopropanol, the mixture was heated to 70°-80° C. and stirred for 2 hours. The internal pressure was then reduced to 5-10 mm Hg to effect stripping for 30 minutes, thus producing an organopolysiloxane polymeric compound as a colorless, easily crushable solid.

Two (2) parts by weight of this organopolysiloxane polymer and 8 parts by weight of dimethylpolysiloxane (viscosity: 5 cs) were mixed to disperse each other, and was thoroughly kneaded by a triple roller to swell, thus producing a silicone gel composition.

Reference Example 4

880 g of dimethylpolysiloxane with dimathylhydrogensilyl terminal groups (Average molecular weight: 2,720; Si-H: 2.6 mol%) and 1,620 g of dimethylmethylvinylpolysiloxane with trimethylsilyl terminal groups (Average molecular weight: 5,000; vinyl group: 1.5 mol%) were mixed, and 0.5 g of 2% chloroplatinic acid solution in isopropanol was added to the mixture. A silicone gel composition was produced from this mixture according to the same procedure as Reference Example 3.

Reference Example 5

55 g of methylhydroxycyclotetrasiloxane (Average molecular weight: 232; Si-H: 50 mol%) and 2,200 g of dimethylpolysiloxane with dimethylvinylsilyl terminal groups (Average molecular weight: 4,400; vinyl group: 1.3 mol%) were mixed, and 0.5 g of 2% chloroplatinic acid solution in isopropanol was added to the mixture. A silicone gel composition was produced from this mixture according to the same manner as in Reference Example 3.

EXAMPLES 1-2

Solid Foundation

Solid foundations having the formulations listed in Table 1 were prepared according to the following method. The feelings on use of the foundations were sensually evaluated. The results are shown in Table 2.

<Formulation>

TABLE 1

| | Examples | | (% parts by weight) Comparative Examples | |
|---|---|---|---|---|
| Component | 1 | 2 | 1 | 2 |
| (1) Liquid paraffin | 36.0 | 36.0 | 36.0 | 64.0 |
| (2) Starch stearic acid ester | 9.0 | 9.0 | 9.0 | 16.0 |
| (3) Pentaerythritol rhodinate | 1.5 | 1.5 | 1.5 | 1.5 |
| (4) Silicone gel composition (produced in Reference Example 1) | 35.0 | — | — | — |
| Silicone gel composition (produced in Reference Example 3) | — | 35.0 | — | — |
| (5) Dimethylpolysiloxane (5 cs) | — | — | 35.0 | — |
| (6) Titanium, dioxide | 12.0 | 12.0 | 12.0 | 12.0 |
| (7) Red iron oxide | 1.2 | 1.2 | 1.2 | 1.2 |
| (8) Yellow iron oxide | 2.7 | 2.7 | 2.7 | 2.7 |
| (9) Black iron oxide | 0.2 | 0.2 | 0.2 | 0.2 |
| (10) Mica | 3.0 | 3.0 | 3.0 | 3.0 |

<Method of Preparation>

Components (1)-(3) were mixed and heated to dissolve. Separately, components (6)-(10) were mixed and pulverized to produce a homogeneous mixture. These mixtures were blended with components (4) or (5) to homogenize and were heated to melt. The product was then charged into a container and solidified to produce a solid foundation.

<Sensory Evaluation>

The solid foundations thus produced were subjected to evaluation tests by 20 female panelists. Each item of the evaluation was rated as follows:

|  | Rating |
|---|---|
| Excellent | 3 |
| Good/Normal | 2 |
| Bad | 1 |

The results of the evaluation was expressed by the following standard:

| | |
|---|---|
| Average rating: more than 2.5 | AAA |
| Average rating: more than 2.0 but not more than 2.5 | BBB |
| Average rating: more than 1.5 but not more than 2.0 | CCC |
| Average rating: not more than 1.5 | DDD |

<Results>

TABLE 2

| Evaluation Item | Example 1 | Example 2 | Comp. Examples 1 | Comp. Examples 2 |
|---|---|---|---|---|
| Lack of Stickiness | AAA | AAA | BBB | BBB |
| Lack of Oiliness | AAA | AAA | DDD | DDD |
| Refreshment | AAA | AAA | DDD | BBB |
| Spreadability | AAA | AAA | AAA | DDD |
| Completeness of make-up | AAA | AAA | DDD | DDD |
| Endurance of make-up | AAA | AAA | DDD | BBB |

The above results evidenced that the solid foundations of this invention exhibited a superior spreadability when they were applied to the skin, providing a smooth, oilless, good feeling to the touch. They did not produce an oily, glittering film, but provided a natural, well-finished make-up. In addition, the cosmetics could be taken out very lightly without giving an heavy feeling with an applicator such as sponge or the like. In contrast, the foundation of Comparative Example 1, although lightly applied onto the skin, was too oily, did not give a close fitness to the skin, and produced a glittering make-up film. The foundation of Comparative Example 2 felt heavy when applied onto the skin and produced a thick make-up film. This foundation did not produce a natural, well-finished make-up.

EXAMPLE 3

Solid Foundation

Solid foundations having the formulations listed in Table 3 were prepared. The feelings on use of the foundations were sensually evaluated. The results are shown in Tables 4-1 and 4-2.

<Formulation>

TABLE 3

| Component | Example 3 | Comparative Examples 3 | 4 | 5 | 6 |
|---|---|---|---|---|---|
| (1) Dextrin stearic acid ester | 6 | 8.34 | 14.8 | 6 | 6 |
| (2) Liquid paraffin | 26 | 36.16 | 64.2 | 26 | 26 |
| (3) Silicone gel composition (produced in Ref. Example 1) | 22 | 22 | — | — | 22 |
| (4) Dimethylpolysiloxane (5 cs) | — | — | — | 22 | — |
| (5) Carboxyvinyl polymer | 0.125 | 0.125 | — | 0.125 | — |
| (6) Sodium hydroxide | 0.025 | 0.025 | — | 0.025 | — |
| (7) Glycerine | 12.5 | — | — | 12.5 | 12.5 |
| (8) Purified water | 12.35 | 12.35 | — | 12.35 | 12.5 |
| (9) Titanium dioxide | 14.5 | 14.5 | 14.5 | 14.5 | 14.5 |
| (10) Inorganic pigment | 1.8 | 1.8 | 1.8 | 1.8 | 1.8 |
| (11) Mica | 4.0 | 4.0 | 4.0 | 4.0 | 4.0 |
| (12) Lecithin | 0.6 | 0.6 | 0.6 | 0.6 | 0.6 |
| (13) Perfume | 0.1 | 0.1 | 0.1 | 0.1 | 0.1 |

<Method of Preparation>

Step A: Mix components (1) and (2) and dissolve the mixture under heating.
Step B: Mix components (5)–(8) to dissolve.
Step C: Mix components (9)–(13) to homogenize and then pulverize the mixture.
Step D: The mixtures obtained in Steps A–C were blended with components (3) or (4) to homogenize by a triple roll mill and were heated to melt. The product was charged into a container and solidified to produce a solid foundation.

<Sensory Evaluation>

The solid foundations thus produced were subjected to evaluation in the same manner as in Examples 1–2.

<Results>

TABLE 4-1

(Immediately after preparation)

| Evaluation Item | Example 3 | Comparative Examples 3 | 4 | 5 | 6 |
|---|---|---|---|---|---|
| Lack of Stickiness | AAA | AAA | CCC | BBB | — |
| Lack of Oiliness | AAA | AAA | DDD | CCC | — |
| Refreshment | AAA | AAA | DDD | BBB | — |
| Spreadability | AAA | AAA | CCC | BBB | — |
| Completeness of make-up | AAA | BBB | BBB | CCC | — |
| Endurance of make-up | AAA | BBB | BBB | CCC | — |

*Components of Comparative Example 6 could not be mixed homogeneously to produce a proper product to be submitted to evaluation.

<Results>

TABLE 4-2

(1 month after preparation stored at room temperature)

| Evaluation Item | Example 3 | Comparative Examples 3 | 4 | 5 | 6 |
|---|---|---|---|---|---|
| Lack of Stickiness | AAA | BBB | CCC | BBB | — |
| Lack of Oiliness | AAA | CCC | DDD | CCC | — |
| Refreshment | AAA | CCC | DDD | BBB | — |
| Spreadability | AAA | BBB | CCC | BBB | — |
| Completeness of make-up | AAA | BBB | BBB | CCC | — |
| Endurance of make-up | AAA | BBB | BBB | CCC | — |

*Components of Comparative Example 6 could not be mixed homogeneously to produce a proper product to be submitted to evaluation.

The above results evidenced that as compared with the foundations of Comparative Examples the foundation of this invention exhibited a superior spreadability when they were applied to the skin, providing a smooth, oilless, good feeling to the touch. They did not produce an oily, glittering film, but provided a natural, well-finished make-up. In addition, the cosmetic of this invention suffered no change over time, thus exhibiting good stability.

EXAMPLE 4-5

Stick Foundation

Stick foundations having the formulations listed in Table 5 were prepared. The feelings on use of the foundations were sensually evaluated. The results are shown in Table 6.

TABLE 5

| | (% parts by weight) | | |
|---|---|---|---|
| | Examples | | Comp. Example |
| Component | 4 | 5 | 7 |
| (1) Microcrystalline wax | 10.0 | 10.0 | 10.0 |
| (2) Pentaerythritol rhodinate | 6.0 | 6.0 | 6.0 |
| (3) Dipentaerythritoltetra-12-hydroxystearic acid sesquistearic acid hemirhodinic acid | 3.0 | 3.0 | 3.0 |
| (4) Glyceryl isostearate | 12.0 | 12.0 | 20.0 |
| (5) Cetyl 2-ethylhexanoate | 6.0 | 6.0 | 6.0 |
| (6) Propylene glycol dicaprate | 9.0 | 9.0 | 9.0 |
| (7) Diglyceryl isostearate | 14.0 | 14.0 | 21.0 |
| (8) Silicone gel composition (produced in Ref. Ex. 1) | 15.0 | — | — |
| Silicone gel composition (produced in Ref. Ex. 3) | — | 15.0 | — |
| (9) Titanium dioxide | 13.0 | 13.0 | 13.0 |
| (10) Red iron oxide | 0.8 | 0.8 | 0.8 |
| (11) Yellow iron oxide | 2.6 | 2.6 | 2.6 |
| (12) Black iron oxide | 0.2 | 0.2 | 0.2 |
| (13) Nylon powder | 5.0 | 5.0 | 5.0 |
| (14) Mica | 5.0 | 5.0 | 5.0 |

<Method of Preparation>

Components (1)–(7), (8), and (9)–(14), mixed and heated separately, were blended under heating, and molded into sticks.

<Sensory Evaluation>

The sticks thus produced were subjected to evaluation in the same manner as in Examples 1-2.

<Results>

TABLE 6

| | (Immediately after preparation) | | |
|---|---|---|---|
| | Examples | | Com. Ex. |
| Evaluation Item | 4 | 5 | 7 |
| Lack of Stickiness | AAA | AAA | BBB |
| Lack of Oiliness | AAA | AAA | BBB |
| Refreshment | AAA | AAA | BBB |
| Spreadability | AAA | AAA | DDD |
| Completeness of make-up | AAA | AAA | DDD |
| Endurance of make-up | BBB | BBB | BBB |

The stick foundations of this invention provided a soft, mild feeling to the touch when they were applied to the skin. The foundation easily spread over the skin and provided an oilless, refreshing feeling upon use. Their make-up effect was excellent. On the other hand, the stick foundation of Comparative Example 7 felt heavy when applied onto the skin and produced a thick make-up film. This stick foundation did not produce a natural, well-finished make-up.

EXAMPLE 6

<Lipstick>

| | (% parts by weight) |
|---|---|
| (1) Microcrystalline wax | 14.0 |
| (2) Pentaerythritol rhodinate | 8.0 |
| (3) Dipentaerythritoltetra-12-hydroxystearic acid sesquistearic acid hemirhodinic acid | 4.0 |
| (4) Glyceryl isostearate | 34.0 |
| (5) Propylene glycol dicaprate | 12.0 |
| (6) Cetyl 2-ethylhexanoate | 6.0 |
| (7) Silicone gel composition (produced in Ref. Ex. 1) | 20.0 |
| (8) D&C Red No. 30 | Suitable amount |
| (9) D&C Red No. 7 | Suitable amount |
| (10) FD&C Yellow No. 5 | Suitable amount |
| (11) Titanated mica | Suitable amount |

<Method of Preparation>

Components (1)–(6), (7), and (8)–(11), mixed and heated separately, were blended under heating, and molded into sticks in the same manner as in Example 1-2.

With the lipstick thus prepared lips could be rouged with an excellent feel to the touch. The lipstick provided soft, smooth feeling, well spread over the lip, and provided an excellent make-up effect.

EXAMPLE 7

Lipstick

A lipstick having the same formulation as that prepared in Example 6, was prepared, except that the silicone gel composition produced in Reference Example 3, instead of that produced in Reference Example 1, was used. The lipstick exhibited a good feeling upon use and its make-up effect was excellent.

EXAMPLE 8

Solid Eye Shadow

<Formulation>

| | (% parts by weight) |
|---|---|
| (1) Dextrin stearic acid ester | 6.4 |
| (2) Glyceryl tripalmitoleate | 1.6 |
| (3) Dipentaerythritoltetra-12-hydroxystearic acid sesquistearic acid hemirhodinic acid | 2.0 |
| (4) Liquid paraffin | 30.0 |
| (5) Silicone gel composition (produced in Ref. Ex. 1) | 30.0 |
| (6) Carboxyvinyl polymer | 0.1 |
| (7) Sodium hydroxide | 0.02 |
| (8) Glycerine | 4.88 |
| (9) D-solbitol | 0.5 |
| (10) Purified water | 5.0 |
| (11) Inorganic colored pigment | 0.2 |
| (12) Organic colored pigment | 1.5 |
| (13) Titanated mica | 13.0 |
| (14) Iron oxide titanated mica | 4.5 |
| (15) Surface active agent | 0.2 |
| (16) Perfume | 0.1 |

<Preparation>

A solid type eye shadow was prepared in the same manner as in Examples 3-4. The eye shadow provided a soft, mild feeling to the touch when they were applied to the skin. The feeling upon use was refreshing and excellent, with no stickiness.

EXAMPLE 9

Rouge

<Formulation>

| | (% parts by weight) |
|---|---|
| (1) Dextrin stearic acid ester | 5.7 |
| (2) Polyisobutylene | 9.7 |
| (3) Glyceryl tripalmitoleate | 2.0 |
| (4) Liquid paraffin | 26.6 |
| (5) Silicone gel composition (produced in Ref. Ex. 3) | 25.0 |
| (6) Carboxyvinyl polymer | 0.1 |
| (7) Sodium hydroxide | 0.02 |
| (8) Glycerine | 5.5 |
| (9) Purified water | 4.38 |
| (10) Nylon fiber powder | 3.0 |
| (11) Mica | 13.71 |
| (12) D&C Red No. 7 | 0.2 |
| (13) Red iron oxide | 0.36 |
| (14) Yellow iron oxide | 0.1 |
| (15) Ultramarine blue | 0.03 |
| (16) Silica | 0.2 |
| (17) Titanated mica | 3.0 |
| (18) Lecithin | 0.4 |

<Preparation> A solid type rouge was prepared in the same manner as in Examples 3-4. The rouge provided a soft, mild feeling to the touch. The feeling upon use was excellent.

EXAMPLE 10

Stick Foundation

<Formulation>

| | (% parts by weight) |
|---|---|
| (1) Microcrystalline wax | 9.0 |
| (2) Pentaerythritol rhodinate | 6.0 |
| (3) Dipentaerythritoltetra-12-hydroxystearic acid sesquistearic acid hemirhodinic acid | 3.0 |
| (4) Glyceryl isostearate | 11.0 |
| (5) Cetyl 2-ethylhexanoate | 5.0 |
| (6) Propylene glycol dicaprate | 8.0 |
| (7) Diglyceryl isostearate | 13.0 |
| (8) Silicone gel composition (produced in Ref. Ex. 1) | 13.0 |
| (9) Carboxyvinyl polymer | 0.2 |
| (10) Sodium hydroxide | 0.04 |
| (11) Purified water | 7.76 |
| (12) Glycerine | 7.0 |
| (13) Titanium dioxide | 12.0 |
| (14) Inorganic colored pigment | 3.5 |
| (15) Mica | 0.3 |
| (16) Perfume | 0.1 |
| (17) UV absorber | 0.1 |
| (18) Surface active agent | 1.0 |

<Preparation>

Step A: Mix components (1)–(7) and (17)–(18) to dissolve under heating.
Step B: Mix components (9)–(12) to dissolve homogeneously.
Step C: Mix components (13)–(16) to homogenize and then pulverize the mixture.
Step D: Homogenize the mixtures obtained in Steps A–C and component (8) with a triple roll mill. The mixture was heated to melt and charged into a container and solidified to produce a stick foundation.

The stick foundation thus prepared gave a soft, mild feeling to the touch. It did not produce an oily, glittering film, but provided a good feeling upon use and excellent make-up effect.

Obviously, numerous modifications and variations of the present invention are possible in light of the above teachings. It is therefore to be understood that within the scope of the appended claims, the invention may be practiced otherwise than as specifically described herein.

What is claimed is:

1. An oily make-up cosmetic comprising:
   (A) an oil base which comprises
      (i) a cosmetically acceptable semi-solid or liquid oil selected from the group consisting of mineral oils, plant oils, animal oils, fatty acids, fatty acid esters and higher alcohols, and
      (ii) 5–40% by weight, based on (A), of a cosmetically acceptable solid oil having a melting point of 40° C. or higher, a cosmetically acceptable oil gelling agent selected from the group consisting of mineral clays, starch fatty acid esters, lipophilic sucrose fatty acid esters, N-acylamino acid amides, N-acylamine acid amine salts, metallic soaps, and a mixture thereof;
   (B) a silicone gel composition which comprises:
      (a) a three-dimensional partially crosslinked organopolysiloxane polymeric compound comprising $R_2SiO$ units and $RSiO_{1.5}$, units, which may also contain $R_3SiO_{0.5}$ units and/or $SiO_2$ units, wherein R independently represents a hydrogen atom, an alkyl group, an aryl group or an unsaturated aliphatic group and the ratio of $R_2SiO$ units to $RSiO_{1.5}$ units is 1:1 to 30:1, or an organopolysiloxane polymeric compound which is insoluble but swells in silicone oil which is prepared by the addition polymerization of (i) an organohydrogenpolysiloxane and (ii) an organopolysiloxane having unsaturated aliphatic groups, wherein the amount of hydrogen and unsaturated aliphatic groups in (i) or (ii) is 1–20 mol% when the organopolysiloxane has a linear or branched structure, and is 1–50 mol% when the organopolysiloxane has a cyclic structure, and contains a partial three dimensional crosslinked structure and
      (b) a silicone oil having a viscosity of about 50 cs or less,
   wherein the weight ratio of (a) and (b) is 5/95 to 30/70, wherein the weight ratio of (A) and (B) is 55/45 to 65/35; and
   (c) a cosmetic powder material.

2. The oily make-up cosmetic according to claim 1, wherein (A) is present in an amount of 30–80 wt.%, (B) is present in an amount of 10–40 wt.% and (C) is present in an amount of 1–40 wt.%.

3. The oily make-up cosmetic according to claim 1, wherein (A) is present in an amount of 40–70 wt.%, (B) is present in an amount of 20–30 wt.% and (C) is present in an amount of 15–25 wt.%.

4. The oily make-up cosmetic according to anyone of claims 1, 2 or 3, wherein the partially cross-linked organopolysiloxane polymeric compound (a) is insoluble in benzene and has a three dimensional structure and in which benzene of an equivalent or more amount of the organopolysiloxane polymeric compound itself may be contained.

5. The oily make-up cosmetic according to claim 1, wherein the weight ratio of (a) and (b) is 10/90 to 25/75.

6. The oily make-up cosmetic according to claim 1, wherein said cosmetic powder material is selected from the group consisting of inorganic white pigment, inorganic colored pigment, organic powder and pearling agent.

7. An oily make-up cosmetic comprising:
(A) an oil base which comprises
   (i) a cosmetically acceptable semi-solid or liquid oil selected from the group consisting of mineral oils, plant oils, animal oils, fatty acids, fatty acid esters and higher alcohols, and
   (ii) 5-40% by weight, based on (A), of a cosmetically acceptable solid oil having a melting point of 40° C. or higher, a cosmetically acceptable oil gelling agent selected from the group consisting of mineral clays, starch fatty acid esters, lipophilic sucrose fatty acid esters, N-acylamino acid amides, N-acylamine acid esters, N-acylamino acid amine salts, metallic soaps, and a mixture thereof;
(B) a silicone gel composition which comprises:
   (a) three-dimensional partially crosslinked organopolysiloxane polymeric compound comprising $R_2SiO$ units and $RSiO_{1.5}$, units, which may also contain $R_3SiO_{0.5}$ units and/or $SiO_2$ units, wherein R independently represents a hydrogen atom, an alkyl group, an aryl group or an unsaturated aliphatic group and the ratio of $R_2SiO$ units to $RSiO_{1.5}$ units is 1:1 to 30:1, or an organopolysiloxane polymeric compound which is insoluble but swells in silicone oil which is prepared by the addition polymerization of (i) an organohydrogenpolysiloxane and (ii) an organopolysiloxane having unsaturated aliphatic groups, wherein the amount of hydrogen and unsaturated aliphatic groups in (i) or (ii) is 1-20 mol% when the organopolysiloxane has a linear or branched structure, and is 1-50 mol% when the organopolysiloxane has a cyclic structure, and contains a partial three dimensional crosslinked structure and
   (b) a silicone oil having a viscosity of about 50 cs or less,
wherein the weight ratio of (a) and (b) is 5/95 to 30/70, wherein the weight ratio of (A) and (B) is 55/45 to 65/35; and
(C) a cosmetic powder material; and
(D) 5-30 wt.%, based on the composition, of an aqueous gel of acrylic water-soluble polymer containing 30-70% by weight of glycerine, said polymer exhibiting a viscosity increase by the addition of an alkali.

8. The oily make-up composition according to claim 7, wherein (A) is present in an amount of 30-80 wt%, (B) is present in an amount of 10-40 Wt.%, (C) is present in an amount of 1-40 Wt.% and (D) is present in an amount of 5-30 wt.%.

9. The oily make-up cosmetic according to claim 7, wherein (A) is present in an amount of 40-70 wt.%, (B) is present in an amount of 20-30 wt.%, (C) is present in an amount of 15-25 wt.% and (D) is present in an amount of 10-25 wt.%.

10. The oily make-up cosmetic according to anyone of claims 7, 8 or 9, wherein the partially cross-linked organopolysiloxane polymeric compound (a) is insoluble in benzene and has a three dimensional structure and in which benzene of an equivalent or more amount of the organopolysiloxane polymeric compound itself may be contained.

11. The oily make-up cosmetic according to claim 7, wherein the weight ratio of (a) and (b) is 10/90 to 25/75.

12. The oily make-up cosmetic according to claim 7, wherein said cosmetic powder material is selected from the group consisting of inorganic white pigment, inorganic colored pigment, organic powder and pearling agent.

13. The oily make-up cosmetic according to claim 7, wherein said solid oil, said oil gelling agent or said mixture thereof comprises 5-40% by weight of said oil base.

* * * * *